United States Patent [19]
Thomas et al.

[11] Patent Number: 5,544,640
[45] Date of Patent: Aug. 13, 1996

[54] SYSTEM AND METHOD FOR HEATING AN OXYGEN SENSOR VIA MULTIPLE HEATING ELEMENTS

[75] Inventors: Christopher P. Thomas, West Bloomfield; Timothy A. Coatesworth, Lake Orion; Kenneth P. DeGroot, Macomb Twp; Jeffery C. Ehlers, Davisburg; Mark E. McMackin, Royal Oak, all of Mich.

[73] Assignee: Chrysler Corporation, Auburn Hills, Mich.

[21] Appl. No.: 498,270

[22] Filed: Jul. 3, 1995

[51] Int. Cl.⁶ ............... F02D 41/14; G01N 27/416
[52] U.S. Cl. ............... 123/689; 123/697; 73/23.32
[58] Field of Search ................ 123/689, 697; 73/23.32; 204/406, 408

[56]  References Cited

U.S. PATENT DOCUMENTS

| | | | |
|---|---|---|---|
| 3,938,479 | 2/1976 | Oberstadt | 123/695 |
| 4,291,572 | 2/1981 | Maufer et al. | 73/23.31 |
| 4,464,244 | 8/1984 | Uchida et al. | 204/425 |
| 4,471,648 | 9/1984 | Uchida et al. | 73/25.03 |
| 4,510,036 | 4/1985 | Takeuchi et al. | 204/425 |
| 4,548,179 | 10/1985 | Ninomiya et al. | 123/697 |
| 4,655,182 | 4/1987 | Nakano et al. | 123/179.1 |
| 4,753,204 | 1/1988 | Kojima et al. | 123/678 |
| 4,808,009 | 2/1989 | Sittler et al. | 374/178 |
| 4,889,098 | 12/1989 | Suzuki et al. | 123/678 |
| 4,963,246 | 10/1990 | Nakajima et al. | 204/406 |
| 4,993,392 | 2/1991 | Tanaka et al. | 73/23.32 |
| 5,245,979 | 9/1993 | Pursifull et al. | 123/690 |
| 5,353,775 | 10/1994 | Yamashita et al. | 123/686 |

*Primary Examiner*—Andrew M. Dolinar
*Attorney, Agent, or Firm*—G. Andrew Barger

[57]  ABSTRACT

A circuit and method are provided for heating a dual heater oxygen sensor. One resistance element is of relatively low resistance such that the oxygen sensor is heated quickly and the other element is of relatively high resistance such that the oxygen sensor is heated and maintained at an optimal operating temperature. The circuit and associated method turn on a low resistance start heater that is in communication with the oxygen sensor given start-up conditions. Once the oxygen sensor has reached an operating temperature range a high resistance operating temperature heater is turned on and the start heater is turned off.

8 Claims, 2 Drawing Sheets

SYSTEM AND METHOD FOR HEATING AN OXYGEN SENSOR VIA MULTIPLE HEATING ELEMENTS

BACKGROUND OF THE INVENTION

The present invention relates, generally, to the art of oxygen sensors. In particular, the present invention relates to heating an oxygen sensor via multiple heating elements each having a different resistance value.

Oxygen sensors are typically employed in a vehicle's exhaust system to sense oxygen so that the fuel air ratio of exhaust gasses emanating from the engine can be calculated by an engine controller. The sensors are placed in the exhaust system of the vehicle, one upstream and one downstream of the catalytic converter, so that the operating efficiency of the catalytic converter may also be monitored via the engine controller. The oxygen sensors have a specific operating temperature range, and may not detect proper amounts of oxygen prior to reaching this range given inherent sensor limitations. Therefore, it is desirable to have the sensors quickly heated, after start-up, to within the operating temperature range thereby allowing for peak operation and oxygen detection.

It has been demonstrated that the oxygen sensors will begin to warm given the heat generated by the engine exhaust. Since the exhaust is relatively cool upon start of the engine, however, the sensors are slow to reach operating temperature range if only the heat of the exhaust is relied upon to heat the sensor. The industry has tried to remedy this by equipping oxygen sensors with a low resistance heating element that is in communication with the inner core element of the oxygen sensor. Since heater performance is inversely proportional to the resistance, the lower the resistance, the quicker the oxygen sensor heater will reach its desired temperature operating range. If the heater is too low in resistance, however, the heater will ramp to high temperature that is out of its operating range. As a result, the inner core element of the sensor may crack or otherwise have a degradation in performance by not giving accurate readings to the engine controller.

Still other oxygen sensor systems supply maximum electrical power to the single heater for a set time after start-up and regulate the power thereafter. This requires the use of costly circuitry for regulating voltage supplied to the heater. Moreover, complex wave shaping circuitry is also required for shaping current waveforms supplied to the sensor heater.

It is therefore desirable in the art of oxygen sensors to have a sensor that heats up quickly to with its temperature operating range and then levels off at a constant temperature for all operating conditions thereafter and that does not require the use of costly, complex voltage and current regulation circuitry.

SUMMARY OF THE INVENTION

In light of such desirable characteristics, not fully present in the related art, the present invention provides a method and system for heating an oxygen sensor via multiple heating elements.

A system for heating an oxygen sensor is provided for an oxygen sensor that has an operating temperature range and an inner core element. The system for heating the oxygen sensor comprises an Electronic Control Unit (ECU) having a microprocessor, memory (volatile and nonvolatile), and at least one data line, the ECU being in electrically operable relation with the oxygen sensor, for selectively applying current to the oxygen sensor. A high resistance heating element which is in communication with the core element is also included. The high resistance element has a first terminal connected to the ECU and a second terminal connected to ground and receives current flow from the ECU when the oxygen sensor is within the operating temperature range. A low resistance heating element which is in communication with the core element and having a first terminal connected to the ECU and a second terminal connected to ground is also provided. The low resistance heating element receives current flow from the ECU when the oxygen sensor is not within the operating temperature range. A method of controlling the operation of a dual heater oxygen sensor is also disclosed.

One object of the present invention is to provide an oxygen sensor that heats up quickly to with its temperature operating range and then levels off at a constant temperature for all operating conditions thereafter.

It is a further purpose of the present invention to employ an oxygen sensor that uses multiple heating elements, each having a different resistance.

It is also an object of the invention to implement an oxygen sensor heating system that does not require the use of costly, complex regulation circuitry.

Another object of the invention is to provide a method for controlling an oxygen sensor having multiple heaters.

Other objects, features and advantages of the present invention will become apparent by reference to the following detailed description when considered in conjunction with the accompanying drawings.

BRIEF DESCRIPTION OF THE DRAWINGS

In the drawings below, reference characters refer to like parts throughout the views, and wherein.

DESCRIPTION OF THE PREFERRED EMBODIMENT(S)

Figure 1:
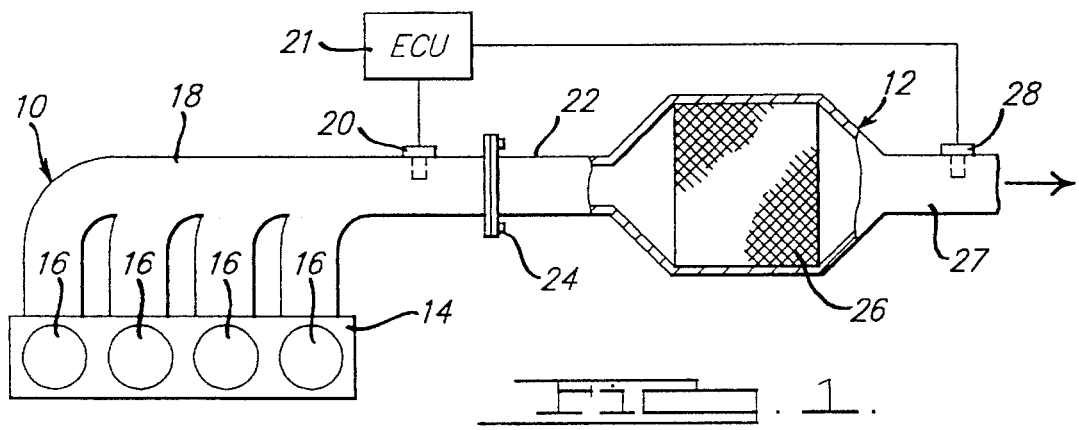
FIG. 1 is a block schematic view of an engine exhaust system and sensor control circuit of the present invention.

Commencing with FIG. 1, an engine exhaust system 10 is shown. An engine block 14 is displayed having four cylinders 16 that emit exhaust gases into the engine manifold 18. It is understood that the present invention will work equally well, regardless of the number of cylinders a particular engine is equipped with. An upstream oxygen sensor 20 is projects into the exhaust manifold 18 for sensing an amount of oxygen present in the exhaust manifold 18. The upstream oxygen sensor 20 is in communication with an Electronic Control Unit (ECU) 21. The ECU 21 has memory (volatile and nonvolatile), software for performing the task of engine control, and at least one data communication line. An engagement seal 24 is provided for sealing engagement of the exhaust manifold 18 to a catalytic converter passageway 22. In operation, the engine exhaust that emanates from cylinders 16 travels through the exhaust manifold 18 and into the catalytic converter passageway 22 whereby the exhaust is partially purified by the catalyst 26 disposed within the catalytic converter 12. The exhaust then passes by a downstream oxygen sensor 28 that projects into the catalytic converter passageway 22. The downstream oxygen sensor 28 is in communication with ECU 21. Finally, the exhaust then exits the vehicle to the atmosphere via a tailpipe (not shown).

Figure 2:
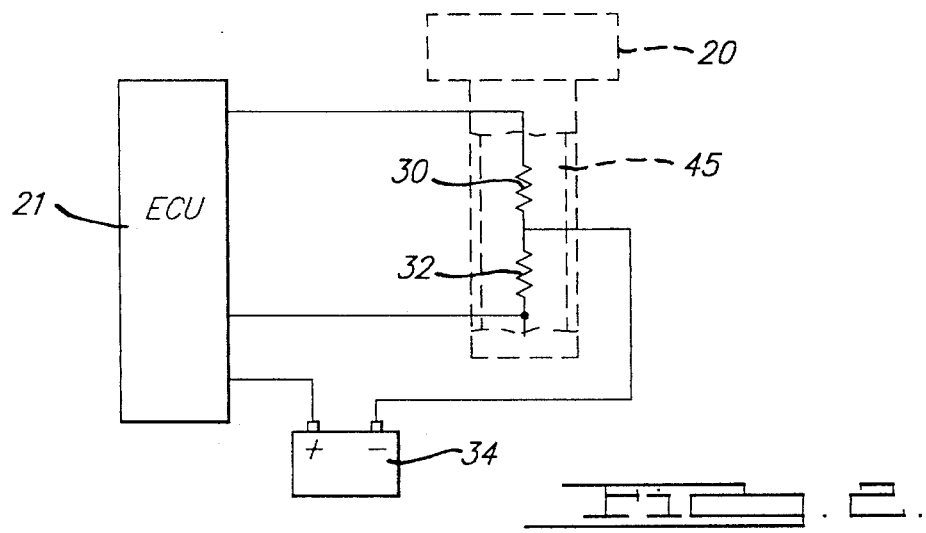
FIG. 2 is a circuit diagram of the present invention.

Referring now to FIG. 2, a circuit for a dual heater oxygen sensor is shown whereby the dual heaters are physically in contact with the oxygen sensor 20 via conductive layers of material. An oxygen sensor 20 is shown in phantom having two heaters, in the form of resistance elements 30, 32, that are in contact with the core element 45 of sensor 20. It is appreciated that the present invention will work equally well given a plurality of oxygen sensors, each having separate connections to ECU 21 and battery 34. In the preferred embodiment, however, only the upstream and downstream oxygen sensors 20, 28 are referenced. Upstream sensor 20 is used as the primary example throughout the figures. Moreover, the term "resistance element" will be used throughout in reference to a DC circuit, it is understood, however, that the elements could also represent an "impedance element" if an AC circuit is employed.

The oxygen sensor 20 has a sensor specific operating temperature range, present designs being in the 900 to 1200 degrees Fahrenheit. The first resistance element 30 is of relatively high resistance of a magnitude greater than or equal to 6 ohms. While resistance element 32 is of relatively low resistance of less than 6 ohms. It is expressly understood, however, that the ohm values of the resistance elements could vary depending on the type of operating temperature range a given oxygen sensor is designed to function under. The operating temperature range is dependent upon the heat conductivity and durability of the core element 45. Moreover, it is also understood that the physical positions of the resistance elements 30, 32 are of no consequence in heating the oxygen sensor 20.

As best shown in FIG. 2, the first terminal of high resistance element 30 is connected to the ECU 21. The second terminal of high resistance element 30 is connected to the negative terminal of battery 34 or ground. Similarly, the first terminal of low resistance element 32 is connected to the ECU 21. While the second terminal of resistance element 32 is connected to the negative terminal of battery 34 or ground. Power is provided to the ECU 21 via the positive terminal of battery 34 that is connected to the ECU 21.

Figure 5:
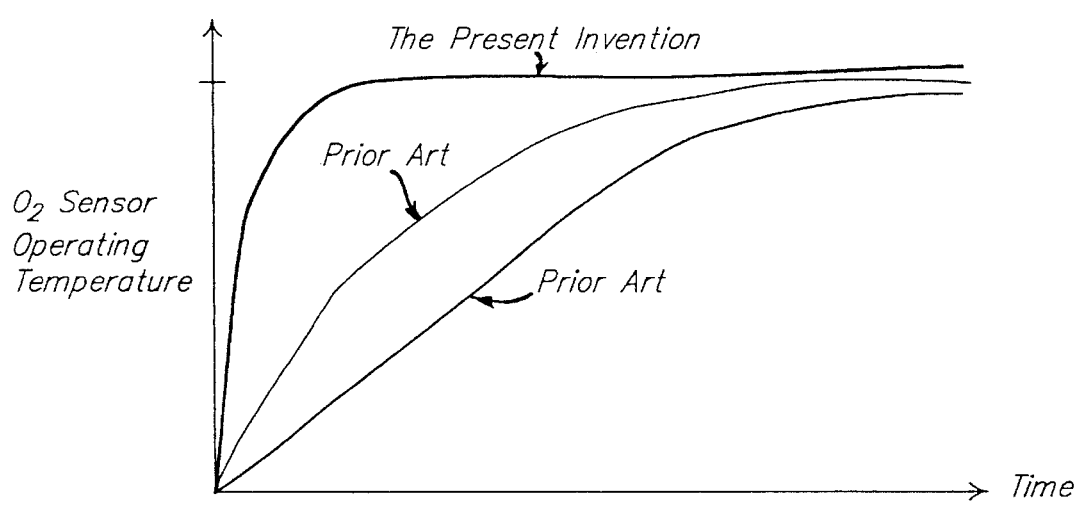
FIG. 5 is a signal wave form diagram illustrating the active temperature curve of an oxygen sensor of the present methodology versus the prior art.

When the vehicle is started, the ECU 21 sends a current signal through low resistance element 32, via the first terminal of low resistance element 32. Current then continues to pass through the low resistance element 32, quickly heating the oxygen sensor 20, until the oxygen sensor 20 reaches its operating temperature range. This is shown in FIG. 5, which shows the relatively quick heating of the oxygen sensor soon after start-up. When the temperature of the oxygen sensor 20 reaches its operating temperature range, the ECU 21 stops sending current to low resistance element 32 and starts sending current to the high resistance element 30. The high resistance element 30 is of such a high resistance level that it maintains the temperature of the sensor 20 within its operating temperature range for the rest of engine operations. This is best shown in FIG. 5, which shows the oxygen sensor temperature curve flattening out at the time the sensor temperature reaches its operating temperature.

Figure 3:
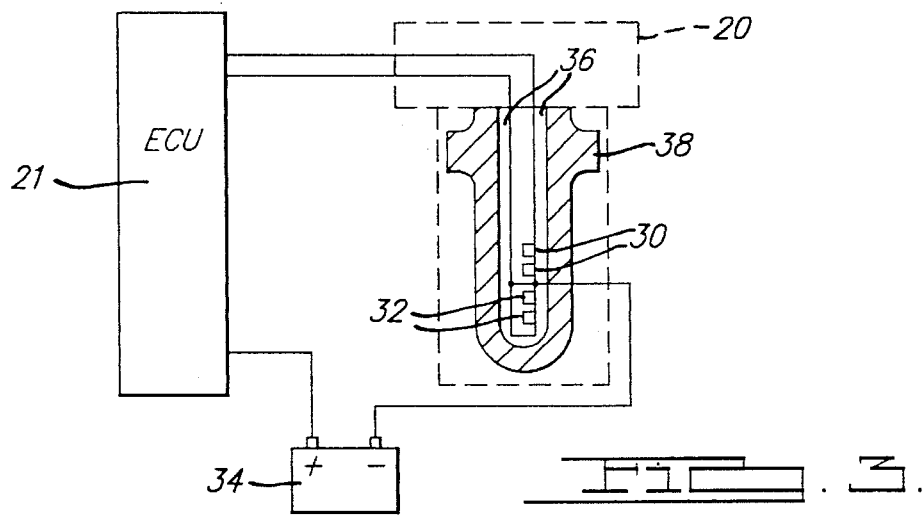
FIG. 3 is a circuit diagram of the present invention.

Referring now to FIG. 3, a circuit for a dual heater oxygen sensor is shown whereby the dual heaters are physically separated from the oxygen sensor 20. An oxygen sensor 20 is shown in phantom having two heaters, in the form of resistance elements 30, 32, that are separated from the core element 38 of sensor 20 via air pockets 36.

The oxygen sensor 20 has a sensor specific operating temperature range, current designs being in the 900° to 1200° degrees Fahrenheit range. The first resistance element 30 is of relatively high resistance of a magnitude greater than or equal to 6 ohms. While resistance element 32 is of relatively low resistance of less than 6 ohms. It is expressly understood, however, that the ohm values of the resistance elements could vary depending on the type of operating temperature range a given oxygen sensor is designed to function under. The operating temperature range is dependent upon the heat conductivity and durability of the core element 38. Moreover, it is also understood that the physical positions of the resistance elements 30, 32 are of no consequence in heating the oxygen sensor 20.

The first terminal of high resistance element 30 is connected to the ECU 21, while the second terminal of high resistance element 30 is connected to the negative terminal of battery 34 or ground. Similarly, the first terminal of low resistance element 32 is connected to the ECU 21. The second terminal of resistance element 32 is connected to the negative terminal of battery 34 or ground. Power is provided to the ECU 21 via the positive terminal of battery 34 that is connected to the ECU 21.

When the vehicle is started, the ECU 21 sends a current signal through the low resistance element 32 via the first terminal of low resistance element 32. Current continues to pass through the low resistance element 32, quickly heating the oxygen sensor 20, until the oxygen sensor 20 reaches it operating temperature range. This is shown in FIG. 5, which shows the relatively quick heating of the oxygen sensor soon after start-up. When the temperature of the oxygen sensor 20 reaches its operating temperature range, the ECU 21 stops sending current to low resistance element 32 and starts sending current to high resistance element 30. The resistance element 30 is of such a high resistance level that it maintains the temperature of the sensor 20 within its operating temperature range for the rest of engine operations. This is best shown in FIG. 5, which shows the oxygen sensor temperature curve flattening out at the time the sensor temperature reaches its operating temperature.

Figure 4:
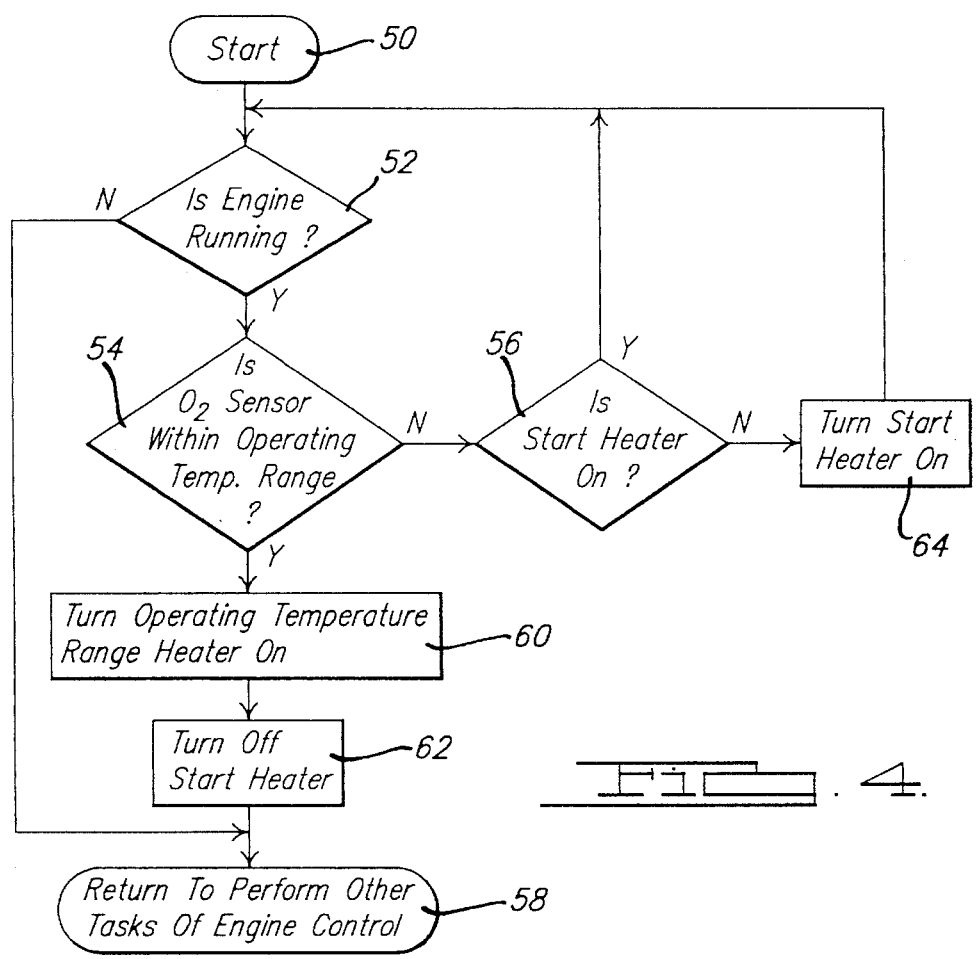
FIG. 4 is a flow chart of a method for heating an oxygen sensor via multiple heating elements of the present invention.

Turning now to FIG. 4, a method for heating an oxygen sensor by using dual heating elements is disclosed. The method starts in bubble 50 and continues to decision block 52. In block 52 it is determined whether at least one enabling engine parameter is met. In the preferred embodiment engine coolant temperature is measured for the engine parameter. It is understood, however, that other engine parameters such as the Manifold Absolute Pressure (MAP), engine speed, or throttle position could also be tested to determine whether they are in a sufficient range for operation of the present method. If the answer in block 52 is no, the method continues to bubble 58 where the method continues to perform others tasks of engine control. If, however, the answer in decision block 52 is yes, the method falls to decision block 54.

In decision block 54 it is determined whether the appropriate oxygen sensor is within operating temperature range. If the answer in block 54 is no, the method falls to decision block 56. In decision block 60 the method determines whether the low resistance heater or start heater is on. If the answer in block 56 is yes, the method returns to test the enabling engine parameters in decision block 52. If the answer in decision block 56 is no, the method determining that the start heater is not on, the method moves to task block 64. In task block 64 the start heater is turned on via the ECU 21 sending a current flow through the resistive element 32. The method then continues to decision block 52 to further test enabling engine parameters.

If, however, the answer in decision block 54 is yes, the method continues on to task block 60. At block 60 the operating temperature range heater, or high resistance element 30, is turned on. The method next falls to task block 62 whereby the start heater 62 is turned off by the ECU 21 stopping the flow of current supplied to low resistance element 32. The method then continues to bubble 58 whereby it returns to perform other tasks of engine control.

While the invention has been described in detail, it is to be expressly understood that it will be apparent to persons skilled in the relevant art that the invention may be modified without departing from the spirit of the invention. Various changes of form, design or arrangement may be made to the invention without departing from the spirit and scope of the invention. Therefore, the above mentioned description is to be considered exemplary, rather than limiting, and the true scope of the invention is that defined in the following claims.

What is claimed is:

1. A system for heating an oxygen sensor, the oxygen sensor having an operating temperature range and an inner core element, the system for heating an oxygen sensor comprising:

an Electronic Control Unit (ECU) having a microprocessor, memory (volatile and nonvolatile), and at least one data line, the ECU in electrically operable relation with the oxygen sensor, for selectively applying current to the oxygen sensor;

a high resistance heating element in communication with the inner core element and having a first terminal connected to the ECU and a second terminal connected to ground, the high resistance heating element receiving current flow from the ECU when the oxygen sensor is within the operating temperature range;

a low resistance heating element in communication with the inner core element and having a first terminal connected to the ECU and a second terminal connected to ground, the low resistance heating element receiving current flow from the ECU when the oxygen sensor is not within the operating temperature range; and a battery having a positive terminal and a negative terminal, the positive terminal connected to the ECU and the negative terminal connected to ground, the battery supplying electrical power to the ECU.

2. The system for heating an oxygen sensor of claim 1, wherein the core element is made of ceramic.

3. The system for heating an oxygen sensor of claim 1, wherein the high resistance element has a resistance value of greater than or equal to 6 ohms.

4. The system for heating an oxygen sensor of claim 1, wherein the low resistance element has a resistance value of less than 6 ohms.

5. A method for heating an oxygen sensor, the oxygen sensor having an operating temperature range, an operating temperature range heater, and a start heater, the method comprising the steps of:

determining whether the oxygen sensor is within the operating temperature range;

turning the operating temperature heater on if the oxygen sensor is within the operating temperature range and turning the start heater off;

determining whether the start heater is on if the oxygen sensor is not within the operating temperature range; and turning the start heater on if the start heater is not on and the oxygen sensor is not within the operating temperature range.

6. The method for heating an oxygen sensor of claim 5 further including the step of returning to determine whether the oxygen sensor is within the operating temperature range if the start heater is on.

7. The method for heating an oxygen sensor of claim 6 further including the step of determining whether at least one engine parameter is met.

8. A method for heating an oxygen sensor, the oxygen sensor having an operating temperature range, an operating temperature range heater, and a start heater, the method comprising the steps of:

checking whether a plurality of enabling engine parameters are met;

returning to perform other tasks of engine control if the plurality of enabling engine parameters are not met;

determining whether the oxygen sensor is within the operating temperature range if the plurality of enabling engine parameters are met;

turning the operating temperature heater on if the oxygen sensor is within the operating temperature range;

turning the start heater off if the oxygen sensor is within the operating temperature range;

returning to perform other tasks of engine control if the oxygen sensor is within the operating temperature range;

determining whether the start heater is on if the oxygen sensor is not within the operating temperature range;

turning the start heater on if the start heater is not on and the oxygen sensor is not within the operating temperature range; and returning to determine whether the oxygen sensor is within the operating temperature range if the start heater is on.

\* \* \* \* \*